(12) United States Patent
Milstein et al.

(10) Patent No.: US 6,844,442 B2
(45) Date of Patent: Jan. 18, 2005

(54) METHOD FOR THE PREPARATION OF METAL CARBENE COMPLEXES

(75) Inventors: David Milstein, Rehovot (IL); Mark Gandelman, Rehovot (IL); Nissan Ashkenazi, Ness Ziona (IL); Boris Rybtchinski, Rehovot (IL)

(73) Assignee: Yeda Research and Development Company, Ltd., Rehovot (IL)

( * ) Notice: Subject to any disclaimer, the term of this patent is extended or adjusted under 35 U.S.C. 154(b) by 0 days.

(21) Appl. No.: 10/474,813

(22) PCT Filed: Apr. 15, 2002

(86) PCT No.: PCT/IL02/00304

§ 371 (c)(1),
(2), (4) Date: Apr. 28, 2004

(87) PCT Pub. No.: WO02/083698

PCT Pub. Date: Oct. 24, 2002

(65) Prior Publication Data

US 2004/0176626 A1 Sep. 9, 2004

(30) Foreign Application Priority Data

Apr. 16, 2001 (IL) .................................................. 142610

(51) Int. Cl.$^7$ ............................. C07F 15/00; C07F 9/22; B01J 31/00
(52) U.S. Cl. ..................... 548/103; 502/152; 556/21; 556/23; 556/136; 556/140; 548/300.1
(58) Field of Search .................... 548/103, 300.1; 556/21, 23, 136, 140; 502/152

(56) References Cited

U.S. PATENT DOCUMENTS

| | | | | |
|---|---|---|---|---|
| 5,831,108 A | | 11/1998 | Grubbs et al. ................ | 556/21 |
| 5,912,376 A | * | 6/1999 | Van Der Schaaf et al. ... | 556/22 |
| 6,504,041 B2 | * | 1/2003 | Grubbs et al. ................ | 556/21 |
| 6,515,084 B2 | * | 2/2003 | Grubbs et al. ................ | 526/90 |
| 6,610,626 B2 | * | 8/2003 | Grubbs et al. .............. | 502/155 |
| 6,613,910 B2 | * | 9/2003 | Grubbs et al. .............. | 548/103 |
| 6,620,955 B1 | * | 9/2003 | Pederson et al. ............. | 556/21 |

OTHER PUBLICATIONS

Abstract: XP–000891602, Schwab, P. et al., "A Series of Well–Defined Metathesis Catalysts Synthesis of [RuCl2 (=CHR') (PR3)2] and Its Reactions", *Angew. Chem. Int. Ed. Engl.*, vol. 34, No. 18, pp. 2039–2041, (1995).

Schwab, P. et al., "Synthesis and Applications of RuCl2 (=CHR') (PR3)2: The Influence of the Alkylidene Moiety on Metathesis Activity", *J. Am. Chem. Soc.*, vol. 118, pp. 100–110, (1996).

Belderrain, T.R. et al., "Reaction between Ruthenium (0) Complexes and Dihalo Compounds. A New Method for the Synthesis of Ruthenium Olefin Metathesis Catalysts", *Organometallics*, vol. 16, pp. 4001–4003, (1997).

Oliván, M. et al., "C–(Halide) Oxidative Addition Routes to Ruthenium Carbenes", *Inorg. Chem.*, vol. 38, pp. 566–570, (1999).

Franzen, V. et al., "Carbene aus Sulfoniumsalzen", *Ber.*, vol. 94, pp. 2942–2950, (1961).

Werner, H. et al., "Stable Osmium Hydrido–Carbene Complexes with CH2 and Secondary Carbenes CHR as Ligands", *Organometallics*, vol. 16, pp. 2236–2238, (1997).

Esteruelas, M.A. et al., "Five– and Six–Coordinate Hydrido (Carbonyl)–Ruthenium (II) and –Osmium (II) Complexes Containing Triisopropylphosphine as Ligand", *J. Organomet. Chem.*, vol. 303, pp. 221–231, (1986).

Abstract: XP–002207330, Vigalok, A. et al., "Direct Synthesis of Thermally Stable PCP–Type Rhodium Carbenes", *Organometallics*, vol. 19, No. 11, pp. 2061–2064, (2000).

Abstract: XP–002207331, Gandelman, M. et al., "A New General Method for the Preparation of Metal Carbene Complexes", *J. Am. Chem. Soc.*, vol. 123, No. 22, pp. 5372–5373, (2001).

* cited by examiner

*Primary Examiner*—Porfirio Nazario-Gonzalez
(74) *Attorney, Agent, or Firm*—Gary M. Nath; Todd L. Juneau; Lee C. Heiman

(57) ABSTRACT

The present invention provides a process for preparing a metal carbene complex of formula (I): wherein M is a transition metal atom selected from the group consisting of ruthenium, rhodium, iron, cobalt, osmium and iridium; L denotes neutral donor ligands ligated to said metal, such groups being the same or different; X is an anionic ligand; R1 and R2 are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl, a is 2 or 3 and b is 1 or 2, such process comprising reacting a sulfur ylide of the formula $Ar_2S=CR^1R^2$ or its precursor with an appropriate metal complex comprising a transition metal atom selected from the group consisting of ruthenium, rhodium, iron, cobalt, osmium and iridium, said metal complex being also in dimeric form, at a temperature between +80° C. and –80° C., in an inert solvent and under inert atmosphere.

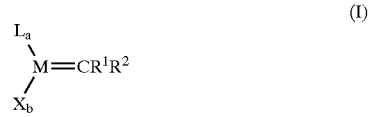

(I)

14 Claims, No Drawings

METHOD FOR THE PREPARATION OF METAL CARBENE COMPLEXES

FIELD OF THE INVENTION

This invention relates to a general method for preparing metal carbene complexes. These complexes may be used, inter alia, to catalyze olefin metathesis reactions, olefin ring opening metathesis polymerization reactions, alkyne metathesis or diolefin cyclization.

BACKGROUND OF THE INVENTION

Alkylidene ligands, such as $CH_2$, CHR, or $CR_2$, form M=C double bonds and their metal compounds are often called metal carbene complexes. The chemistry of late-transition-metal (i.e. groups VIII, IX and X of the periodic table) carbene complexes has recently received much attention, primarily due to the high catalytic activity of phosphine ruthenium carbene complexes in olefin metathesis. The most useful ruthenium carbene in these series is Grubbs' catalyst, $(PCy_3)_2Cl_2Ru$=CHPh, bearing a benzylidene unit (Schwab P. et al., Angew. Chem. Int. Ed. Engl. 1995, 34, 2039; Schwab P. et al., J. Am. Chem. Soc. 1996, 118, 100, U.S. Pat. No. 5,831,108). Being highly active and remarkably tolerant to common functional groups, this compound found broad applications in both organic and polymer chemistry.

There are several synthetic approaches towards alkylidene complexes, with the ones utilizing the corresponding diazoalkane being the most popular and most general (Schwab P. et al., J. Am. Chem. Soc. 1996, 118, 100). However, the instability of diazo compounds and the safety issues involved in handling them seriously limit this method. From safety considerations it is also difficult to use such diazo compounds in industry.

Another recent approach, involving the reaction of precursors to unstable Ru(0) complexes with alkyl dihalides ((a) Belderrain, T. R.; Grubbs, R. H. *Organometallics* 1997, 16, 4001. (b) Olivan, M.; Caulton, K. G. *Inorg. Chem.* 1999, 38, 566) is limited by the difficult synthesis of the unstable Ru(COD)(COT) precursor.

SUMMARY OF THE INVENTION

In view of the above, it is desired to provide a new method for the preparation of metal carbene complexes which is general, synthetically simple and safe.

Thus, the present invention describes a new method for the preparation of metal carbene complexes by using sulfur ylides as carbenoid precursors. Such ylides are extensively used in organic chemistry. The new synthetic route is synthetically simple and safe and can be applied to complexes of different metals and different ligands. Moreover, it can be used for the synthesis of new carbenes, which are difficult to obtain by known methods.

The metal carbene complexes are powerful catalysts in organic synthesis and may be used, inter alia, to catalyze olefin metathesis reactions, olefin ring opening metathesis polymerization reactions, alkyne metathesis, diolefin cyclization and olefin cyclopropanation.

According to a first of its aspects, the present invention provides a process for preparing a metal carbene complex of the formula (I)

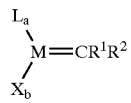

wherein

M is a transition metal atom selected from the group consisting of ruthenium, rhodium, iron, cobalt, osmium and iridium L denotes neutral donor ligands ligated to said metal, such groups being the same or different;

X is an anionic ligand;

$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl, a is 2 or 3 and b is 1 or 2, such process comprising reacting a sulfur ylide of the formula $Ar_2S$=$CR^1R^2$ or its precursor wherein each Ar is independently selected from aryl, substituted aryl, and aryl or substituted aryl bound to a polymeric unit, with an appropriate metal complex comprising a transition metal atom selected from the group consisting of ruthenium, rhodium, iron, cobalt, osmium and iridium, at least two neutral ligands capable of forming donor bonds with said metal and at least one further organic or anionic inorganic group which form a complex with said metal, said metal complex being also in dimeric form, at a temperature between +80° C. and −80° C., preferably between +50° C. and −50° C., in an inert solvent and under inert atmosphere, to give the metal carbene complex of formula (I).

Examples of preferable metal complexes are shown in the following Scheme 1.

Scheme 1:
Examples of preferable metal complexes

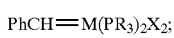

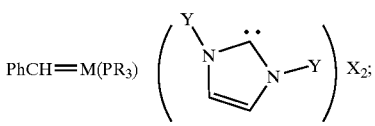

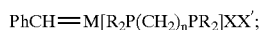
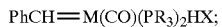
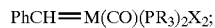

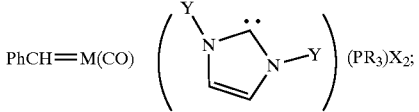

M = Ru, Os; R = Phenyl, Isopropyl, t-Butyl, Cyclohexyl; n = 1, 2, 3;
X = F, Cl, Br; X' = $PF_6$, $BF_4$, $BPh_4$, $ClO_4$, $CF_3SO_3$;
Y = Me, iPr, t-Bu -continued PhCH=M(PR₃)₂X;

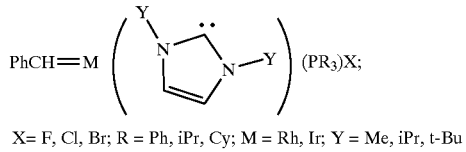

X= F, Cl, Br; R = Ph, iPr, Cy; M = Rh, Ir; Y = Me, iPr, t-Bu

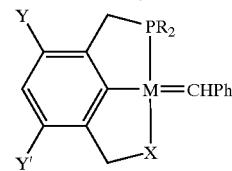

M-Rh, Ir; X = PR₂, NEt₂; R = iso-Propyl, t-Butyl, Y, Y' = H, Me

According to a preferred embodiment, in the above metal carbene of formula (I) M is ruthenium or osmium. In such case the metal carbene has the general formula:

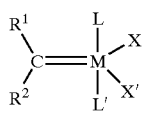

including isomers thereof, wherein

L and L' are independently selected from nucleophilic carbene, phosphine, amine, imine, CO, sulfide, thiol, heteroaryl wherein the heteroatom is either nitrogen or sulfur, or L and L' are bonded together to form a multidentate ligand;

X and X' are independently selected from the group consisting of halide, cyano, and carboxylate or one of X or X' may also be an anion selected from $PF_6^-$, $BF_4^-$, $BPh_4^-$, $ClO_4^-$, $CF_3SO_3^-$, alkyl and perfluoroalkyl sulfonate;

$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

The nucleophilic carbene has the following general formula:

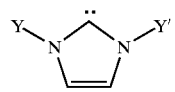

wherein

Y and Y' are independently selected from the group consisting of hydrogen, substituted or unsubstituted alkyl, substituted or unsubstituted cycloalkyl, substituted or unsubstituted alkenyl, substituted or unsubstituted aryl, aralkyl, and each carbon of the double bond may be optionally substituted.

Alternatively, the metal carbene has the general formula:

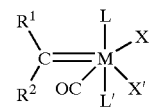

including isomers thereof, wherein

L and L' are independently selected from nucleophilic carbene, phosphine, amine, imine, thiol, sulfide, heteroaryl wherein the heteroatom is either nitrogen or sulfur or L and L' are bonded together to form a bidentate ligand;

X and X' are independently selected from the group consisting of hydrogen, halide, cyano and carboxylate or one of X or X' may also be an anion selected from $PF_6^-$, $BF_4^-$, $BPh_4^-$, $ClO_4^-$, $CF_3SO_3^-$, alkyl and perfluoroalkyl sulfonate;

$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

The above nucleophilic carbene has the general formula:

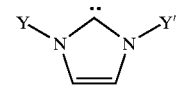

wherein

Y and Y' are independently selected from the group consisting of hydrogen, substituted or unsubstituted alkyl, substituted or unsubstituted cycloalkyl, substituted or unsubstituted alkenyl, substituted or unsubstituted aryl, aralkyl, and each carbon of the double bond may be optionally substituted.

According to another embodiment, in the above metal carbene of formula (I) M is rhodium or iridium. In such case the metal carbene has the general formula:

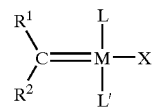

including isomers thereof, wherein

L and L' are independently selected from nucleophilic carbene, phosphine, amine, imine, CO, sulfide, thiol, heteroaryl wherein the heteroatom is either nitrogen or sulfur or L and L' are bonded together to form a bidentate ligand;

X is selected from the group consisting of halide, cyano, carboxylate, $PF_6^-$, $BF_4^-$, $BPh_4^-$, $ClO_4^-$; alkyl sulfonate or when X is bonded to L and/or L', then it may also be substituted or unsubstituted alkyl or substituted or unsubstituted aryl;

$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

DETAILED DESCRIPTION OF THE INVENTION

According to a first of its aspects, the present invention provides a general method for the preparation of metal carbene complexes. The general pathway is presented in Scheme 2.

Scheme 2

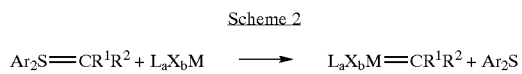

A specific example of the process of the present invention is shown in Scheme 3 below. According to this scheme, benzyldiphenylsulfonium tetrafluoroborate 1, the precursor of the corresponding ylide compound, is prepared by a one-pot reaction between diphenylsulfide and benzyl bromide in the presence of $AgBF_4$ (Franzen, V.; Schmidt, H. J.; Mertz, C. Ber., 1961, 94, 2942). Deprotonation of this sulfonium salt by base, results in the formation of the benzyl ylide 2, that readily reacts with the appropriate metal complex to give the metal carbene complex $L_aX_bM=CHPh$.

Scheme 3

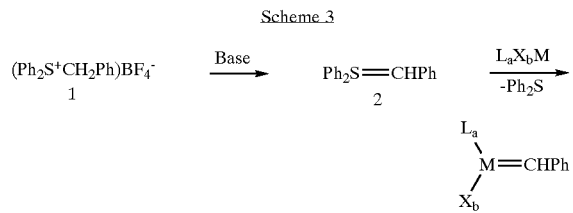

In another example, at least one of the phenyl groups in 1, bound to the sulfur, may be linked to an insoluble polymeric unit, for example polystyrene or a non-organic polymer such as silica. In such cases after the reaction is complete, the diphenyl sulfide linked to the insoluble polymer unit is separated by filtration from the metal carbene complex $L_aX_bM=CHPh$ and re-used.

More specifically, when the sulfonium salt 1 is reacted with 1 equiv. of $KN(SiMe_3)_2$ at −30° C. in toluene, immediate formation of a yellow solution and precipitation of $KBF_4$ takes place (Scheme 4). After filtration of $KBF_4$, the formed sulfur ylide 2 is reacted with a complex 3a or 3b under a nitrogen atmosphere and at −30° C. resulting in clean conversion to the Rh-benzylidene complex 4a or 4b, respectively. The Rh(I) benzylidene complexes are not stable at room temperature and were characterized by multinuclear NMR spectroscopy at −40° C. The carbene protons in the $^1H$ NMR spectrum are characterized by low-field signals (e.g. between 17 and 20 ppm), due to coupling with the Rh center. The carbenoid carbons also give rise to extremely low field signals in $^{13}C$ NMR spectrum, between 270 and 350 ppm.

Scheme 4

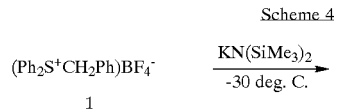

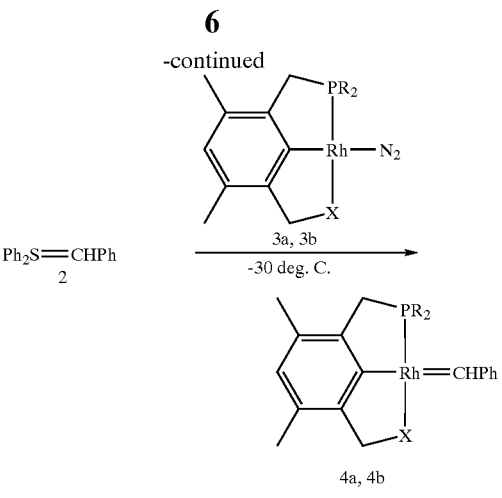

compounds 3a, 4a:
R = $^i$Pr, X = P($^i$Pr)$_2$
compounds 3b, 4b:
R = $^t$Bu, X = NEt$_2$ (In the Scheme above, $^i$Pr denotes an isopropyl radical; $^t$Bu denotes a tert-butyl radical)

The above compounds of formulae 3a, 3b, 4a and 4b are new and present a further aspect of the invention.

Stable, well-known metal carbenes can also easily and cleanly be prepared by the sulfur ylide approach described in the present invention. An example is the preparation of the synthetically very useful Grubbs' catalyst, $(PCy_3)_2Cl_2Ru=CHPh$ (5) (Cy denotes a cyclohexyl radical). The reaction of $(PPh_3)_3RuCl_2$ in $CH_2Cl_2$ with the freshly prepared sulfur ylide 2 in THF at −30° C. and concomitant substitution of the $PPh_3$ ligands by tricyclohexylphosphine at room temperature results, after the workup, in the Ru-benzylidene complex 5 in 98% yield (Scheme 5).

The process of the present invention is not limited to rhodium and ruthenium carbenes, see for example Werner's hydrido-osmium carbene 6 (Werner H. et al., Organometallics, 1997, 16, 2236) shown in Scheme 5. According to this scheme, ylide 2 is added to the osmium complex $[OsHCl(CO)(P^iPr_3)_2]$ (Esteruelas, M. A.; Werner, H. J. Organomet. Chem. 1986, 303, 22)1 in toluene at −30° C., resulting in an immediate color change to orange. Stirring for additional 30 min. at room temperature and workup results in quantitative formation of the benzylidene complex 6, as evident from its spectroscopic data compared to the literature.

Scheme 5

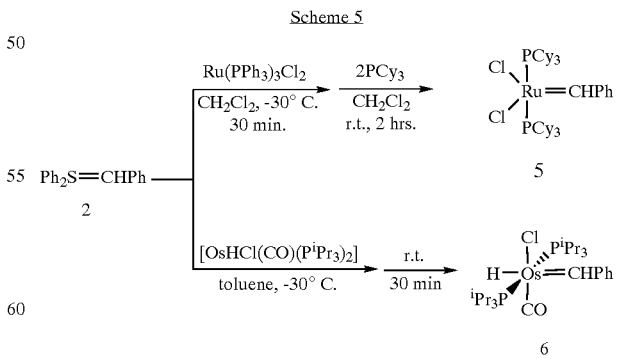

The process of the present invention can be applied also to the synthesis of unknown carbenes, which are difficult to obtain by methods known in the art. For example, the carbene complexes trans-[RhCl(=CRR')($P^iPr_3$)$_2$] have been prepared in the literature by an indirect route with the aid of SbR$_3$ ligands, which were subsequently substituted by the bulky triisopropylphosphine ligands. However, attempts to prepare similar monosubstituted carbene trans-[RhCl (=CHPh)(P$^i$Pr$_3$)$_2$] by use of phenyldiazomethane didn't lead to the desired results. Remarkably, this complex may be synthesized by the new process of the invention and without the aid of stibine ligands (see Scheme 6).

Thus, the monosubstituted carbene trans-[RhCl(=CHPh) (P$^i$Pr$_3$)$_2$] is prepared as follows: bis-(triisopropylphosphine) rhodium chloride dimer 7 reacts with one equiv. of the sulfur ylide 2 at −30° C. in toluene, followed by selective formation of the Rh benzylidene complex 8 (Scheme 6).

Scheme 6

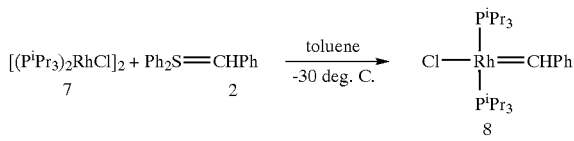

Compound 8 is moderately stable and decomposes at room temperature within 3–4 days.

The present invention is now described by the following non-limiting examples.

EXAMPLES

All experiments below were performed under an inert nitrogen atmosphere.

Example 1

Reaction of 3a with Ph$_2$SCHPh. Formation of Complex 4a

A toluene solution (3 ml) of KN(SiMe$_3$)$_2$ (27 mg, 0.133 mmol) was added dropwise to a stirred suspension of [Ph$_2$SCH$_2$Ph]BF$_4$ (48 mg, 0.132 mmol) in 2 ml of toluene at −30° C. The resulting yellow solution was filtered into a toluene solution of 3 (60 mg, 0.132 mmol) precooled to −30° C. A color change from brown to dark green-brown took place upon warming up of the mixture to room temperature. $^{31}$P{$^1$H} NMR revealed formation of complex 4a in almost quantitative yield. Complex 4a is stable at temperatures below −30° C. and was spectroscopically characterized at −40° C.

Characterization of 4a (toluene-d$_8$) $^{31}$P{$^1$H} NMR 71.90 (d, $^1$J$_{RhP}$=165.0 Hz). $^1$H NMR 19.75 (d, $^2$J$_{RhH}$=2.7 Hz, 1H, Rh=CHPh), 8.18 (d, J$_{HH}$=7.1 Hz, 2H, Ar—H), 7.32 (d, J$_{HH}$=8.1 Hz, 2H, Ar—H), 7.16 (m, 4H, Ar—H), 3.29 (vt, J$_{HH}$=4.2 Hz, 4H, Ar—CH$_2$-P), 1.70 (m, 4H, CH(CH$_3$)$_2$), 0.91 (m, 24H, CH(CH$_3$)$_2$).

Selected $^{13}$C{$^1$H} NMR signals: 340.80 (m, Rh=CHPh), 182.60 (dt, J$_{RhC}$=19.4 Hz, J$_{PC}$=10.0 Hz, C$_{ipso}$).

Example 2

Reaction of 3b with Ph$_2$SCHPh. Formation of Complex 4b

To a stirred suspension of [Ph$_2$SCH$_2$Ph]BF$_4$ (48 mg, 0.132 mmol) in 2 ml of toluene was added a solution of KN(SiMe$_3$)$_2$ (27 mg, 0.133 mmol) in 3 ml of toluene at −30° C. The resulting yellow solution of 2 was filtered into a cold (−30° C.) toluene solution of 3b (63 mg, 0.132 mmol). The reaction mixture was warmed to the room temperature and an almost quantitative conversion to complex 4a was observed by $^{31}$P{$^1$H} NMR. Compound 4b was not stable at room temperature and was characterized at −40° C.

Characterization of 4b (toluene-d$_8$) $^{31}$P{$^1$H} NMR 92.72 (d, $^1$J$_{RhP}$=218.23 Hz). $^1$H NMR: 17.21 (d, $^2$J$_{RhH}$=7.8 Hz, 1H, Rh=CHPh), 8.37 (d, J$_{HH}$=7.6 Hz, 2H, Ar—H), 7.75 (m, 1H, Ar—H), 7.53 (d, 1H, J=7.3 Hz Ar—H), 7.12 (m, 1H, Ar—H), 6.63 (bs, 1H, Ar—H) 3.99 (s, 2H, Ar—CH$_2$—N), 3.63 (bd, 2H, J$_{PH}$=8.4 Hz, Ar—CH$_2$—P), 3.03 (m, 2H, N—CH$_2$—CH$_3$), 2.92 (m, 2H, N—CH$_2$—CH$_3$), 2.84 (m, 6H, N—CH$_2$—CH$_3$), 2.39 (s, 3H, Ar—CH$_3$), 2.19 (s, 3H, Ar—CH$_3$), 1.23 (d, 18H, J$_{PH}$=12.6 Hz, C(CH$_3$)$_3$).

Selected $^{13}$C{$^1$H} NMR signals: 283.51 (m, Rh=CHPh), 186.15 (dd, J$_{RhC}$=18.6 Hz, J$_{PC}$=9.4 Hz, C$_{ipso}$), 32.41 (d, J$_{PC}$=16.3 Hz, P—C(CH$_3$)$_3$).

Example 3

Preparation of 5

[Ph$_2$SCH$_2$Ph]BF$_4$ (53 mg, 0.146 mmole) was dissolved in THF (3 ml) and cooled to −30° C. A solution of KN(SiMe$_3$)$_2$ (35 mg, 0.146 mmole) in THF (1 ml) was added, resulting in a rapid change of color to yellow. The yellow solution was added, at −30° C., to a solution of Ru(PPh$_3$)$_3$Cl$_2$ (138 mg, 0.144 mmole) in CH$_2$Cl$_2$ (5 ml). The mixture was kept at −30° C. for an additional 30 min. A solution of tricyclohexylphosphine (88 mg, 0.310 mmol) in CH$_2$Cl$_2$ (5 ml) was then added and the mixture was warmed up to room temperature and stirred for 2 hrs. The solvent was removed under vacuum and the residue was washed with methanol (3×10 ml) to remove the residual phosphine, sulfide and silyl by products. The remaining solid was dried under high vacuum to give the clean Grubss' carbene 5 (130 mg, 0.141 mmol) in 98% yield as evident from its spectral data compared to the literature.

Example 4

Preparation of 6

A toluene solution (3 ml) of KN(SiMe$_3$)$_2$ (27 mg, 0.133 mmol) was added dropwise to a suspension of [Ph$_2$SCH$_2$Ph] BF$_4$ (48 mg, 0.132 mmol) in 2 ml of toluene at −30° C. The resulting yellow solution was filtered into a cold (−30° C.) toluene solution of [OsHCl(CO)(P$^i$Pr$_3$)$_2$] (75 mg, 0.132 mmol). After the reaction mixture was stirred for 30 min., the solvent and volatile products were removed under high vacuum. The product was extracted from dry residue with ether (3×4 ml) and solvent was evaporated resulting in compound 6 as an orange solid.

Example 5

Preparation of 8

Complex 8 was prepared analogously to complexes 4, using 30 mg (0.033 mmol) of dimer 7, 24 mg (0.066 mmol) of [Ph$_2$SCH$_2$Ph]BF$_4$ and 14 mg (0.066 mmol) of KN(SiMe$_3$)$_2$.

Characterization of 8 (toluene-d$_8$) $^{31}$P{$^1$H} NMR 32.10 (d, $^1$J$_{RhP}$=167.4 Hz). $^1$ $^{NMR:}$ 20.17 (dt, $^2$J$_{RhH}$=3.2 Hz, $^3$J$_{PH}$=6.1 Hz, 1H, Rh=CHPh), 8.12 (d, J$_{HH}$=7.2 Hz, 1H, Ar—H), 7.30–6.92 (m, 4H, Ar—H), 2.21 (m, 6H, CH(CH$_3$)$_2$), 1.83 (m, 36H, CH(CH$_3$)$_2$). $^{13}$C NMR: 317.86 (m, Rh=CHPh), 25.53 (vt, CH(CH$_3$)$_2$), 20.34 (s, CH(CH$_3$)$_2$).

Example 6

Preparation of (PCy$_3$)$_2$Cl$_2$Ru=CHCH=CH$_2$ (This complex was previously reported by Schwab, P.; Grubbs, R. H, Ziller, J. W. *J. Am. Chem. Soc.* 1996, 118, 100)

($Ph_2S^+CH_2CH=CH_2$)$BF_4^-$(10 mg, 0.032 mmol) was suspended in THF (3 ml) and cooled to $-35°$ C. A solution of potassium bis(trimethylsilyl)amide (7 mg, 0.035 mmol) in THF (2 ml) was added to the suspension of the sulfonium salt, followed by rapid color change to yellow. The yellow solution was filtered through cotton directly into a solution at $-35°$ C., of tris(triphenylphosphine)ruthenium dichloride (30 mg, 0.031 mmol) in THF (5 ml). A solution of tricyclohexylphosphine (18 mg, 0.064 mmol) in THF (2 ml) precooled to $-35°$ C. was then added, and the mixture was kept for 2 h at $-35°$ C. and then warmed to room temperature and kept at room temperature for 20 min. The solvent was removed under vacuum and the residue was extracted with pentane. The pentane extract was filtered and evaporated resulting in a red solid.

$^{31}P\{^1H\}$ NMR in $C_6D_6$ (singlet at 37.9 ppm) and $^1H$ NMR in $C_6D_6$ (doublet at 17.9 ppm, J=10.3 Hz) spectra of this solid indicated that the expected allyl carbene ruthenium complex was formed, in addition to impurities of $PPh_3$ and $PCy_3$.

What is claimed is:

1. A process for preparing a metal carbene complex of the formula (i)

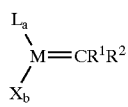

(I)

wherein
M is a transition metal atom selected from the group consisting of ruthenium, rhodium, iron, cobalt, osmium and iridium;
L denotes neutral electron donor ligands ligated to said metal, such groups being the same or different;
X is an anionic ligand;
$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted of unsubstituted aryl, substituted or unsubstituted heteroaryl, substituted or unsubstituted vinyl,
a is 2 or 3 and
b is 1 or 2,
such process comprising reacting a sulfur ylide of the formula $Ar_2S=CR^1R^2$ or its precursor, wherein each Ar is independently selected from aryl, substituted aryl, and aryl or substituted aryl bound to a polymeric unit, with an appropriate metal complex comprising a transition metal atom selected from the group consisting of ruthenium, rhodium, iron, cobalt, osmium and iridium, at least two neutral ligands capable of forming donor bonds with said metal and at least one further organic or inorganic anionic group which form a complex with said metal, including dimers of such metal complex, at a temperature between $+80°$ C. and $-80°$ C., in an inert solvent and under inert atmosphere, to give the metal carbene complex of formula (i).

2. A process according to claim 1, carried out at a temperature between $+50°$ C. and $-50°$ C.

3. A process according to claim 1, wherein said metal carbene of the formula (i) is prepared in a one pot reaction starting from a compound of formula $Ar_2SCHR^1R^2$, where Ar, $R^1$ and $R^2$ are as defined in claim 1, which is deprotonated under base conditions to form the ylide of the formula $Ar_2S=CR^1R^2$ which is then reacted according to claim 1.

4. A process according to claim 1, wherein M is selected from ruthenium and osmium.

5. A process according to claim 4, wherein said metal carbene has the formula:

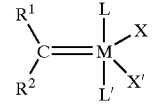

including isomers thereof, wherein
L and L' are independently selected from nucleophilic carbene, phosphine, amine, imine, CO, sulfide, thiol, heteroaryl wherein the heteroatom is either nitrogen or sulfur, or L and L' are bonded together to form a multidentate ligand;
X and X' are independently selected from the group consisting of halide, cyano, and carboxylate or one of X or X' may also be an anion selected from $PF_6^-$, $BF_4^-$, $BPh_4^-$, $ClO_4^-$, $CF_3SO_3^-$, alkyl sulfonate and perfluoroalkyl sulfonate;
$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

6. A process according to claim 5 wherein said nucleophilic carbene has the formula;

wherein
Y and Y' are independently selected from the group consisting of hydrogen, substituted or unsubstituted alkyl, substituted or unsubstituted cycloalkyl, substituted or unsubstituted alkenyl, substituted or unsubstituted aryl, aralkyl, and each carbon of the double bond may be optionally substituted.

7. A process according to claim 4, wherein said metal carbene has the formula

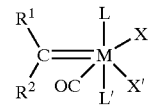

including isomers thereof, wherein
L and L' are independently selected from nucleophilic carbene, phosphine, amine, imine, CO, sulfide, thiol, heteroaryl wherein the heteroatom is either nitrogen or sulfur or L and L' are bonded together to form a bidentate ligand;
X and X' are independently selected from the group consisting of hydrogen, halide, cyano and carboxylate or one of X or X' may also be an anion selected from $PF_6^-$, $BF_4^-$, $BPh_4^-$, $ClO_4^-$, $CF_3SO_3^-$, alkyl sulfonate and perfluoroalkyl sulfonate;
$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

8. A process according to claim 1 wherein M is selected from rhodium and iridium.

9. A process according to claim 8, wherein said metal carbene has the formula:

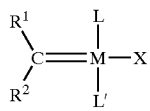

including isomers thereof, wherein

L and L' are independently selected from nucleophilic carbene, phosphine, amine, imine, CO, sulfide, thiol, heteroaryl wherein the heteroatom is either nitrogen or sulfur or L and L' are bonded together to form a bidentate ligand;

X is selected from the group consisting of halide, cyano, carboxylate, $PF_6^-$, $BF_4^-$, $BPh_4^-$, $ClO_4^-$, $CF_3SO_3^-$, alkyl sulfonate and perfluoroalkyl sulfonate or when X is bonded to L and/or L', then it may also be substituted or unsubstituted alkyl or substituted or unsubstituted aryl;

$R^1$ and $R^2$ are each independently selected from the group consisting of hydrogen, substituted or unsubstituted C1–C20 alkyl, substituted or unsubstituted C2–C20 alkenyl, substituted or unsubstituted cycloalkyl, substituted or unsubstituted heterocycloalkyl, substituted or unsubstituted aryl, substituted or unsubstituted heteroaryl, substituted or unsubstituted vinyl.

10. A process according to claim 9, wherein said nucleophilic carbene substituent is of the formula:

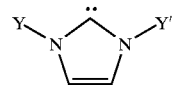

wherein

Y and Y' are independently selected from the group consisting of hydrogen, substituted or unsubstituted alkyl, substituted or unsubstituted cycloalkyl, substituted or unsubstituted alkenyl, substituted or unsubstituted aryl, aralkyl, and each carbon of the double bond may be optionally substituted.

11. A process according to claim 1 wherein said sulfur ylide has the formula $Ph_2S=CR^1R^2$ or its precursor and the transition metal atom in the metal complex is selected from the group consisting of ruthenium, rhodium, osmium and iridium.

12. A process according to claim 1, wherein at least one Ar group in said sulfur ylide of the formula $Ar_2S=CR^1R^2$ is bound to polystyrene.

13. A rhodium complex of the formula:

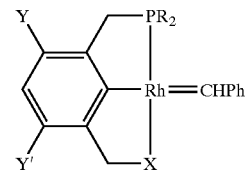

wherein R is alkyl or aryl, X is an amine moiety and Y and Y' are independently selected from H or alkyl.

14. A compound according to claim 13, wherein R is t-butyl, Y and Y' are independently selected from H and alkyl and X is diethylamine.

* * * * *